(12) United States Patent
Roger et al.

(10) Patent No.: US 10,874,463 B2
(45) Date of Patent: Dec. 29, 2020

(54) BONE SCREW AND INSTRUMENTS FOR PROBING POSITION OF BONE SCREW

(71) Applicant: SPINAL DEVELOPMENTS PTY LTD, St Leonards (AU)

(72) Inventors: Gregory James Roger, Milsons Point (AU); Davor Drago Saravanja, East Lindfield (AU)

(73) Assignee: SPINAL DEVELOPMENTS PTY LTD., St Leonards (AU)

( * ) Notice: Subject to any disclaimer, the term of this patent is extended or adjusted under 35 U.S.C. 154(b) by 36 days.

(21) Appl. No.: 15/756,165

(22) PCT Filed: Sep. 1, 2016

(86) PCT No.: PCT/AU2016/050822
§ 371 (c)(1),
(2) Date: Feb. 28, 2018

(87) PCT Pub. No.: WO2017/035592
PCT Pub. Date: Mar. 9, 2017

(65) Prior Publication Data
US 2018/0289429 A1    Oct. 11, 2018

(30) Foreign Application Priority Data
Sep. 1, 2015   (AU) ............................... 2015903562

(51) Int. Cl.
*A61B 34/20*    (2016.01)
*A61B 17/70*    (2006.01)
*A61B 90/00*    (2016.01)

(52) U.S. Cl.
CPC .......... *A61B 34/20* (2016.02); *A61B 17/7032* (2013.01); *A61B 17/7037* (2013.01);
(Continued)

(58) Field of Classification Search
CPC ...... A61B 6/4417; A61B 5/0555; A61B 90/39
See application file for complete search history.

(56) References Cited

U.S. PATENT DOCUMENTS

| | | | | |
|---|---|---|---|---|
| 5,551,429 A | * | 9/1996 | Fitzpatrick | A61B 6/12 600/426 |
| 2004/0167391 A1 | * | 8/2004 | Solar | A61B 90/39 600/411 |

(Continued)

FOREIGN PATENT DOCUMENTS

| | | |
|---|---|---|
| EP | 2910206 A1 | 8/2015 |
| WO | 2004075768 A2 | 9/2004 |

(Continued)

OTHER PUBLICATIONS

European Search Report for EP 16840421.

*Primary Examiner* — Ellen C Hammond
*Assistant Examiner* — Tara Rose E Carter
(74) *Attorney, Agent, or Firm* — Browdy and Neimark, PLLC

(57) ABSTRACT

The present disclosure relates to polyaxial bone screws and methods that enable the positioning of the polyaxial bone screws to be reliably determined using a surgical navigation system including a navigation probe. In an embodiment, a polyaxial bone screw comprises a threaded shaft inserted in bone and a head connected to the shaft, the head being rotatable relative to the shaft about a centre of rotation of the head of the bone screw. The position of a navigation probe is monitored using a navigation device. A first mating surface of the head of the bone screw is engaged with a second mating surface of the navigation probe; and the location of the centre of rotation of the head of the bone screw is determined based on the monitored position of the (Continued)

navigation probe when the first mating surface and the second mating surface are engaged.

17 Claims, 11 Drawing Sheets

(52) U.S. Cl.
CPC ......... *A61B 2034/2055* (2016.02); *A61B 2034/2057* (2016.02); *A61B 2034/2065* (2016.02); *A61B 2034/2072* (2016.02); *A61B 2090/3762* (2016.02)

(56) References Cited

U.S. PATENT DOCUMENTS

| | | | |
|---|---|---|---|
| 2004/0254576 A1* | 12/2004 | Dunbar, Jr. | A61B 17/7091 606/914 |
| 2007/0043378 A1 | 2/2007 | Kumar et al. | |
| 2010/0234891 A1 | 9/2010 | Freeman et al. | |
| 2011/0218546 A1 | 9/2011 | De la Fuente Klein et al. | |
| 2012/0035669 A1 | 2/2012 | Jackson | |
| 2012/0232377 A1* | 9/2012 | Nottmeier | A61B 6/0492 600/411 |
| 2013/0325075 A1 | 12/2013 | Jackson | |

FOREIGN PATENT DOCUMENTS

| | | |
|---|---|---|
| WO | 2015003224 A1 | 1/2015 |
| WO | 2016041001 A1 | 3/2016 |

\* cited by examiner

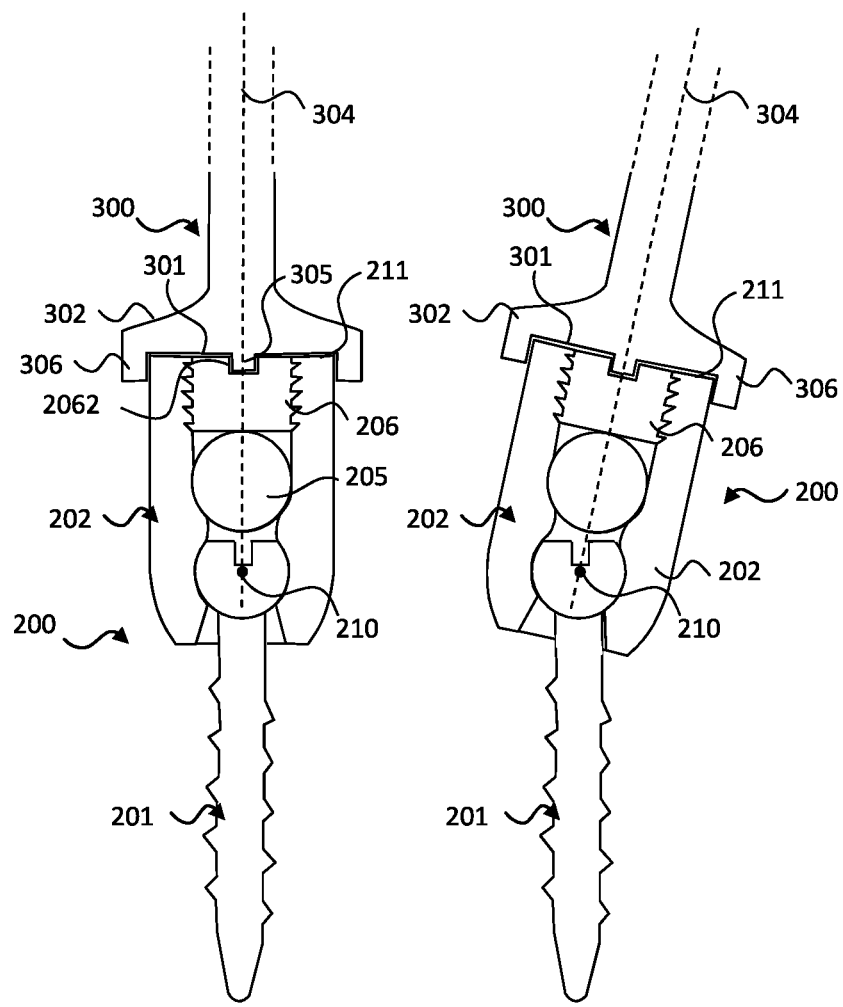

BONE SCREW AND INSTRUMENTS FOR PROBING POSITION OF BONE SCREW

CROSS-REFERENCE TO RELATED APPLICATIONS

The present application claims priority from Australian Provisional Patent Application No. 2015903562 filed on 1 Sep. 2015, the content of which is incorporated herein by reference.

TECHNICAL FIELD

The present disclosure relates to devices and methods used in surgery such as spinal surgery. The device and methods aid in reliable navigation of the anatomical and surgical landscape.

BACKGROUND

Surgery, such as implant surgery and in particular spinal implant surgery, requires knowledge of the anatomy of the patient which can often be distorted through degeneration, deformity, neoplasia or trauma. An ability to navigate safely around the anatomy throughout a surgical procedure is desirable.

While experience can allow a surgeon or surgical team to perform procedures without the assistance of aids, this experience can take some time to accumulate. In less experienced hands, as well as for more complex cases with grossly distorted anatomy, a number of navigation systems have been devised to help make the surgery more reliable and safe. An example includes computer assisted surgery, in which a computer tomograph (CT) scan of an anatomical structure is used to assist the surgery.

In spinal surgery, scans are performed once the patient is positioned on the operating table and the spinal column has been operatively exposed. This allows navigation equipment to be attached to a nearby bony structure so that a mobile CT scanner can scan both the spine and the navigation equipment with the resultant images fed to a navigation system to allow guidance during surgery.

Despite the fact that the patient is positioned on an operating table and is relatively motionless, there is nevertheless motion between the vertebrae. This can be caused by respiration, movement of the table itself, motion caused by retractors and other surgical instruments and inadvertent disturbance of the navigational equipment by the surgical team.

As a consequence fiducial markers are desirable in spinal surgery to allow confirmation of the accuracy of the navigation information as surgery progresses. Such fiducial markers can be temporarily inserted onto one or more vertebrae and can also be inserted into bone that is not to be removed surgically. A navigation probe can be used to touch and probe the fiducial markers and compare their position with that shown by the navigation system.

Additionally or alternatively, apparatus that is implanted in the patient can be used, in effect, as fiducial markers. For example, fixation devices, such as pedicle screws fixed to vertebrae can be used as fiducial screws. Moreover, by registering the position of fixation devices, the location of the fixation devices may be introduced to the images of the navigation system. Still further, registering of the positions of the fixation device can allow a determination of an appropriate configuration for a bone rod or plate to engage with the fixation devices to be carried out with greater ease.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY

Aspects of the present disclosure provide surgical systems, apparatus, devices and methods that enable the positioning of a polyaxial bone screw, e.g. of a type to be inserted in a vertebra, to be reliably determined using a surgical navigation system including a navigation probe. The surgical systems, apparatus, devices and methods may be used in spinal surgery or other types of surgery that employ bone screws. Once determined, the position may be registered in an image of the anatomy that is prepared via a pre-operative or intra-operative scan, for example.

A polyaxial bone screw commonly includes a threaded shaft for insertion in bone and a head connected to the shaft, the head being rotatable relative to the shaft. The head is rotatable (e.g., by tilting and/or swivelling) about multiple axes with a common centre of rotation. When the screw is inserted in bone, usually the only accessible part of the bone screw is the head. The position of the shaft remains substantially fixed relative to the bone; however, the head is rotatable relative to the bone. Therefore, using the navigation probe to probe a point on the outside of the head of the screw does not necessarily provide a sufficiently accurate indication of the position of the bone screw relative to the bone, or the position of the bone to which the screw is fixed, for all surgical navigation purposes. The present inventors have determined, however, that the centre of rotation of the head of the bone screw, which centre of rotation remains in a constant position relative the shaft of the bone screw, can provide a reliable reference point of a polyaxial bone screw for surgical navigation purposes. The present disclosure describes, inter alia, techniques for probing a centre of rotation of the head of the bone screw and other reference points.

According to one aspect, the present disclosure provides a method of determining the position of a polyaxial bone screw during surgery using a surgical navigation system, wherein the polyaxial bone screw comprises a threaded shaft inserted in bone and a head connected to the shaft, the head being rotatable relative to the shaft about a centre of rotation of the head of the bone screw, and wherein the method comprises:

monitoring the position of a navigation probe using a navigation device of the surgical navigation system;

engaging a first mating surface of the head of the bone screw with a second mating surface of the navigation probe;

determining the location of the centre of rotation of the head of the bone screw based on the monitored position of the navigation probe when the first mating surface and the second mating surface are engaged.

The bone screw and navigation probe may be configured such that, when the first and second mating surfaces are engaged, at all rotational positions of the head of the bone screw relative to the shaft, a probe axis of the navigation probe has a fixed orientation relative to the head of the bone screw, and the second mating surface of the navigation probe is at a constant distance from the centre of rotation of the head of the bone screw.

According to one aspect, the present disclosure provides a surgical navigation system comprising:
a polyaxial bone screw, the polyaxial bone screw comprising:
a threaded shaft for insertion in bone; and
a head connected to the shaft, the head being rotatable relative to the shaft about a centre of rotation of the head of the bone screw;
a navigation probe for probing the position of the bone screw, the navigation probe having a probe axis;
wherein the head of the bone screw comprises a first mating surface and the navigation probe comprises a second mating surface adapted to engage the first mating surface,
wherein the bone screw and navigation probe are configured such that, when the first and second mating surfaces are engaged, at all rotational positions of the head of the bone screw relative to the shaft:
the probe axis of the navigation probe has a fixed orientation relative to the head of the bone screw, and
the second mating surface of the navigation probe is at a constant distance from the centre of rotation of the head of the bone screw.

According to another aspect, the present disclosure provides a polyaxial bone screw, the polyaxial bone screw comprising:
a threaded shaft for insertion in bone; and
a head connected to the shaft, the head being rotatable relative to the shaft about a centre of rotation of the head of the bone screw;
the head comprising a first mating surface adapted to engage a second mating surface of a navigation probe for probing the position of the bone screw; wherein, when the first and second mating surfaces are engaged, at all rotational positions of the head of the bone screw relative to the shaft:
the probe axis of the navigation probe has a fixed orientation relative to the head of the bone screw, and
the second mating surface of the navigation probe is at a constant distance from the centre of rotation of the head of the bone screw.

According to another aspect, the present disclosure provides a navigation probe comprising:
a second mating surface adapted to engage a first mating surface of a polyaxial bone screw, the polyaxial bone screw comprising:
a threaded shaft for insertion in bone; and
a head connected to the shaft, the head being rotatable relative to the shaft about a centre of rotation of the head of the bone screw;
wherein the head comprises the first mating surface; and
wherein, when the first and second mating surfaces are engaged, at all rotational positions of the head of the bone screw relative to the shaft:
the probe axis of the navigation probe has a fixed orientation relative to the head of the bone screw, and
the second mating surface of the navigation probe is at a constant distance from the centre of rotation of the head of the bone screw.

The method, system and devices of the above aspects can be used to determine the position of a navigational reference point of the bone screw. The reference point may be the centre of rotation of the head of the bone screw or a reference point having a fixed positional relationship with the centre of rotation the bone screw. When the first and second mating surfaces are engaged, the reference point may be calculated based on a determination of (i) the orientation of the navigation probe and the position of the second mating surface; and (ii) the distance between the first or second mating surface and the centre of rotation of the head of the bone screw. Since the second mating surface is engaged with the first mating surface, the distance between the second mating surface and the centre of rotation of the head of the bone screw will substantially correspond to the distance between the first mating surface and the centre of rotation of the head of the bone screw. The distance between the first mating surface and the centre of rotation of the head of the bone screw may be determined based on known or measured dimensions of the bone screw.

The orientation of the navigation probe and the position of its second mating surface may be determined using components of a surgical navigation system, including a navigation device and a processor. The navigation device may comprise a camera, e.g. an infrared (IR) camera, which can monitor changes in position of the probe. The navigation device may provide a form of input device to the processor. The processor may comprise processing units and/or other appropriate electronic circuitry. The probe may comprise or support one or more reflective components, such as reflective balls. The reflective components may be designed to reflect light of a particular frequency, for example infrared (IR), such that the camera (e.g. an IR camera) can remotely detect the position of the probe.

When the reference point for the bone screw is determined, the position of the reference point may be overlaid or registered by the processor on an image of the patient's anatomy to assist with surgical navigation. The image may be prepared pre-operatively and/or intra-operatively by a computed tomography (CT) device, a MRI device and/or an X-ray device and/or any other means of generating scaleable images or representations of the anatomy.

According to one aspect, a method of determining the position of a polyaxial bone screw during surgery using a surgical navigation system is provided, wherein the polyaxial bone screw comprises a threaded shaft inserted in bone and a head connected to the shaft, the head being rotatable relative to the shaft about a centre of rotation of the head of the bone screw, and wherein the method comprises:
receiving positional data indicative of the orientation of a navigation probe and a position of a second mating surface of the navigation probe, when the second mating surface is engaged with a first mating surface of the head of the bone screw; and
determining the position of a navigational reference point of the bone screw based on the received positional data and a known distance between the first or second mating surface and the centre of rotation of the head of the bone screw.

According to one aspect there is provided a machine-readable medium comprising instructions stored therein, which when executed by a processor, causes the processor to perform the method of the preceding aspect.

In preceding aspects, the navigation probe may be elongate having an axis of elongation, the probe axis corresponding to the axis of elongation. The probe axis may extend through a grip portion, e.g. a handle region, at a proximal end of the navigation probe, and through a tip of the navigation probe at a distal end of the navigation probe. The second mating surface may be provided at the tip of the navigation probe. In some embodiments, when the first and second mating surfaces are engaged, and at all positions of the head of the bone screw relative to the shaft, the probe axis may extend through the centre of rotation of the head of the bone screw.

As indicated, the tip of the navigation probe may comprise the second mating surface. The second mating surface may therefore be a distal end surface of the navigation probe. The second mating surface of the navigation probe may extend along a plane that is perpendicular to the probe axis, for example.

The first mating surface may be provided by all or part of a top surface of the head of the bone screw, for example. The head of the bone screw may comprise a head body adapted to receive a bone rod. For example, the head body may be substantially U-shaped or "tulip-shaped" body, such as to define a recess to receive the rod. The head may further comprise a locking cap operable to bear down on a top surface of the rod and lock the rod in position in the recess of the head body. When the locking cap bears against the rod, a top surface of the locking cap may be substantially aligned with a top surface of the head body. The top surface of the head of the bone screw may comprise the top surface of the head body and/or the top surface of the locking cap.

When the first and second mating surfaces are engaged, the first and second mating surfaces may abut each another in a substantially parallel relationship. The first and second mating surfaces may have only one clear position of engagement, where the first and second mating surfaces rest against each other with a tight fit, ensuring that the navigation probe axis maintains a fixed orientation relative to the head of the bone screw when engagement takes place.

The first and second mating surfaces may comprise first and second complimentary interlocking features adapted to engage each other. The first interlocking features may comprise recesses such as bores, holes or dimples and the second interlocking features may comprise complimentary protrusions such as pegs, bumps or pins adapted to locate in the recesses. The first interlocking features may be comprised in the first mating surface and the second interlocking features may be comprised in the second mating surface. Nevertheless, the positioning of the first and second interlocking features may be reversed, or both first and second interlocking features may be comprised in each of the first and second mating surfaces. The first and second mating surfaces may comprise, in combination, one, two, three or more first interlocking features and a complimentary number of second interlocking features.

The first and second mating surfaces may have relatively broad surface areas that abut against each other. Alternatively, separate, distinct points of engagement may be made between the first and second mating surfaces only. The separate, distinct points of engagement may be provided via the interlocking features as described above, for example, or otherwise. Where separate, distinct points of engagement are relied upon, at least three separate, distinct points of engagement may be provided in order to ensure that the probe axis of the navigation probe maintains a fixed orientation relative to the head of the bone screw when the engagement takes place.

The second mating surface of the navigation probe may comprise an outer flange that projects from a periphery of the second mating surface. The outer flange may be annular. The outer flange may be adapted to extend around a periphery of the first mating surface when the first and second mating surfaces are engaged. The outer flange may define a recess of the navigation probe that receives the top of the head of the bone screw therein, for example, when the first and second mating surfaces are engaged.

While, in aspects above, the reference point of the bone screw may be determined through one act of engagement between the navigation probe and the head of the bone screw, in alternative aspects a similar result may be achieved through successive engagements between the navigation probe and different marker points on the head of the bone screw.

According to one aspect, the present disclosure provides a method of determining the position of a polyaxial bone screw during surgery using a surgical navigation system, wherein the polyaxial bone screw comprises a threaded shaft inserted in bone and a head connected to the shaft, the head being rotatable relative to the shaft about a centre of rotation of the head of the bone screw, and wherein the method comprises:

monitoring the position of a navigation probe;

successively engaging the navigation probe with at least first, second and third marker points on a surface of the head of the bone screw, the first, second and third marker points being separated from each other and each being located at a respective constant distance from the centre of rotation of the head of the bone screw at all rotational positions of the head relative to the shaft;

determining the location of each of the first, second and third marker points based on the monitored position of the navigation probe when engaged with the first, second and third marker points; and determining the centre of rotation of the head of the bone screw based on the determined locations of the first, second and third marker points.

According to one aspect, the present disclosure provides a surgical navigation system comprising:

a polyaxial bone screw, the polyaxial bone screw comprising:
  a threaded shaft for insertion in bone; and
  a head connected to the shaft, the head being rotatable relative to the shaft about a centre of rotation of the head of the bone screw; and
a navigation probe for probing the bone screw;
wherein the head of the bone screw comprises at least first, second and third marker points on a surface thereof, each marker point being engageable with the navigation probe to determine the location of the marker point, wherein the first, second and third marker points are separated from each other and are each located at a respective constant distance from the centre of rotation of the head of the bone screw at all rotational positions of the head relative to the shaft.

According to another aspect, the present disclosure provides a polyaxial bone screw, the polyaxial bone screw comprising:

a threaded shaft for insertion in bone; and
a head connected to the shaft, the head being rotatable relative to the shaft about a centre of rotation of the head of the bone screw;
wherein the head of the bone screw comprises at least first, second and third marker points on a surface thereof, each marker point being engageable with a navigation probe to determine the location of the marker point, wherein the first, second and third marker points are separated from each other and are each located at a respective constant distance from the centre of rotation of the head of the bone screw at all rotational positions of the head relative to the shaft.

The method, system and device of the above aspects can be used to determine the position of a navigational reference point of the bone screw. The reference point may be the centre of rotation of the head of the bone screw or a reference point having a fixed positional relationship with the centre of rotation of the head of the bone screw. Once the locations of the first second and third marker points have been determined, the reference point may be determined based on a triangulation calculation. The calculation may be based on the determined locations of the first, second and third marker points and a known, fixed spatial relationship between each of the first, second and third marker points and the centre of rotation of the head of the bone screw.

The position of the navigation probe may again be determined using a surgical navigation system including a navigation device and a processor as described above. Moreover, when the reference point for the bone screw is determined, the position of the reference point may be reproduced or registered on an image of the patient's anatomy to assist with surgical navigation as described above.

In the aspects that use first, second and third marker points, the navigation probe need not have a fixed orientation relative to the head of the bone screw when engaged with the first, second and third marker points. This may provide advantages when the surgical environment limits probe access to the bone screw, for example. Moreover, a generic navigation probe may be used, rather than a navigation probe that may be modified to co-apt with a specific mating surface of the head of the bone screw, for example.

According to one aspect, a method of determining the position of a polyaxial bone screw during surgery using a surgical navigation system is provided, wherein the polyaxial bone screw comprises a threaded shaft inserted in bone and a head connected to the shaft, the head being rotatable relative to the shaft about a centre of rotation of the head of the bone screw, and wherein the method comprises:

receiving positional data indicative of positions of a navigation probe when it successively engages with at least first, second and third marker points on a surface of the head of the bone screw; and determining the position of a navigational reference point of the bone screw based on the received positional data and a known positional relationship between each of the first, second and third marker points and the centre of rotation of the head of the bone screw.

According to one aspect there is provided a machine-readable medium comprising instructions stored therein, which when executed by a processor, causes the processor to perform the method of the preceding aspect.

In the preceding aspects, any one or more of the first, second and third marker points may comprise a dimple or other type of recess on the surface of the head of the bone screw, enabling a tip of the navigation probe to positively engage therewith. Nevertheless, one or more of the marker points may take alternative forms, such as protrusions or painted or etched indicia on the surface.

One or more of the first second and third marker points may be located on a top surface of the head of the bone screw. For example, they may be located at spaced positions on a substantially annular portion of the top surface of the bone screw that surrounds a locking cap.

While, in aspects above, a reference point of the bone screw, such as the centre of rotation, is determined through probing at least three marker points of the bone screw, in alternative embodiments a reduced number of marker points may be probed. For example, only a single marker point may be probed and an approximation of the location of the centre of rotation may be made on this basis.

Thus, according to one aspect, the present disclosure provides a method of determining the position of a polyaxial bone screw during surgery using a surgical navigation system, wherein the polyaxial bone screw comprises a threaded shaft inserted in bone and a head connected to the shaft, the head being rotatable relative to the shaft about a centre of rotation of the head of the bone screw, and wherein the method comprises:

monitoring the position of a navigation probe;

engaging the navigation probe with at least a first marker point on a surface of the head of the bone screw, the first marker point being located at a constant distance from the centre of rotation of the head of the bone screw at all rotational positions of the head relative to the shaft;

determining the location of the first marker point based on the monitored position of the navigation probe when engaged with the first marker point; and determining an approximate position of a reference point of the bone screw based on the determined location of the first marker point.

According to one aspect, the present disclosure provides a surgical navigation system comprising:

a polyaxial bone screw, the polyaxial bone screw comprising:
  a threaded shaft for insertion in bone; and
  a head connected to the shaft, the head being rotatable relative to the shaft about a centre of rotation of the head of the bone screw;
a navigation probe for probing the bone screw;
wherein the head of the bone screw comprises at least a first marker point on a surface thereof, the first marker point being located at a constant distance from the centre of rotation of the head of the bone screw at all rotational positions of the head relative to the shaft, the first marker point being engageable with the navigation probe to determine the location of the first marker point.

According to another aspect, the present disclosure provides a polyaxial bone screw, the polyaxial bone screw comprising:

a threaded shaft for insertion in bone; and
a head connected to the shaft, the head being rotatable relative to the shaft about a centre of rotation of the head of the bone screw;
wherein the head of the bone screw comprises at least a first marker point on a surface thereof, the first marker point being located at a constant distance from the centre of rotation of the head of the bone screw at all rotational positions of the head relative to the shaft, the first marker point being engageable with a navigation probe to determine the location of the first marker point.

The method, system and device of the above aspects can be used to determine an approximate position of a navigational reference point of the bone screw. The reference point may be the centre of rotation of the head of the bone screw, a reference point having a fixed positional relationship with the centre of rotation of the head of the bone screw or otherwise. Once the location of the first marker point has been determined, the position of the reference point may be estimated based on a known, fixed spatial relationship between the first marker point and the reference point. The estimation may also take into account an approximate orientation of the navigation probe when engaged with the first marker point. This approximation may be based on a pre-agreed approximate orientation that a surgeon should hold the navigation probe when engaging it with the first marker point. As one example, the surgeon may be directed to hold the probe such that the probe axis points towards the centre of rotation of the head of the bone screw when engaged with the first marker point.

According to one aspect, a method of determining the position of a polyaxial bone screw during surgery using a surgical navigation system is provided, wherein the polyaxial bone screw comprises a threaded shaft inserted in bone and a head connected to the shaft, the head being rotatable relative to the shaft about a centre of rotation of the head of the bone screw, and wherein the method comprises:

receiving positional data indicative of the positioning of a navigation probe when it engages with at least a first marker point on a surface of the head of the bone screw; and determining the position of a navigational reference point of the bone screw based on the received positional data and a known distance between the first marker point and the centre of rotation of the head of the bone screw.

According to one aspect there is provided a machine-readable medium comprising instructions stored therein, which when executed by a processor, causes the processor to perform the method of the preceding aspect.

Aspects and embodiments of the present disclosure may allow an instantaneous analysis of screw positioning to be made (particularly adjacent the surface of bone, for example) and/or an analysis of movement of screw positioning over time to be made. An indication of the orientation of the head of the bone screw may also be obtained. However, in some instances, the apparatus described may not enable an indication of the orientation of the shaft of the bone screw to be accurately determined. To enable shaft orientation to be determined, an indexing device may be provided. The indexing device may include a protractor or other type of angle measuring device, for example. The indexing device may be mounted via a collar to the shaft of the bone screw, for example. The indexing device may be releasable from the shaft after use.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF DESCRIPTION OF DRAWINGS

By way of example only, embodiments of the present disclosure are now described with reference to the accompanying drawings in which:

FIGS. 4a and 4b show cross-sectional views of a tip of a navigation probe engaged with the polyaxial bone screw of FIG. 2 at different rotation positions;

FIG. 7b shows a top view of the polyaxial bone screw of FIG. 7a;

FIG. 12b shows a top view of the polyaxial bone screw of FIG. 12a;

DESCRIPTION OF EMBODIMENTS

Figure 1:
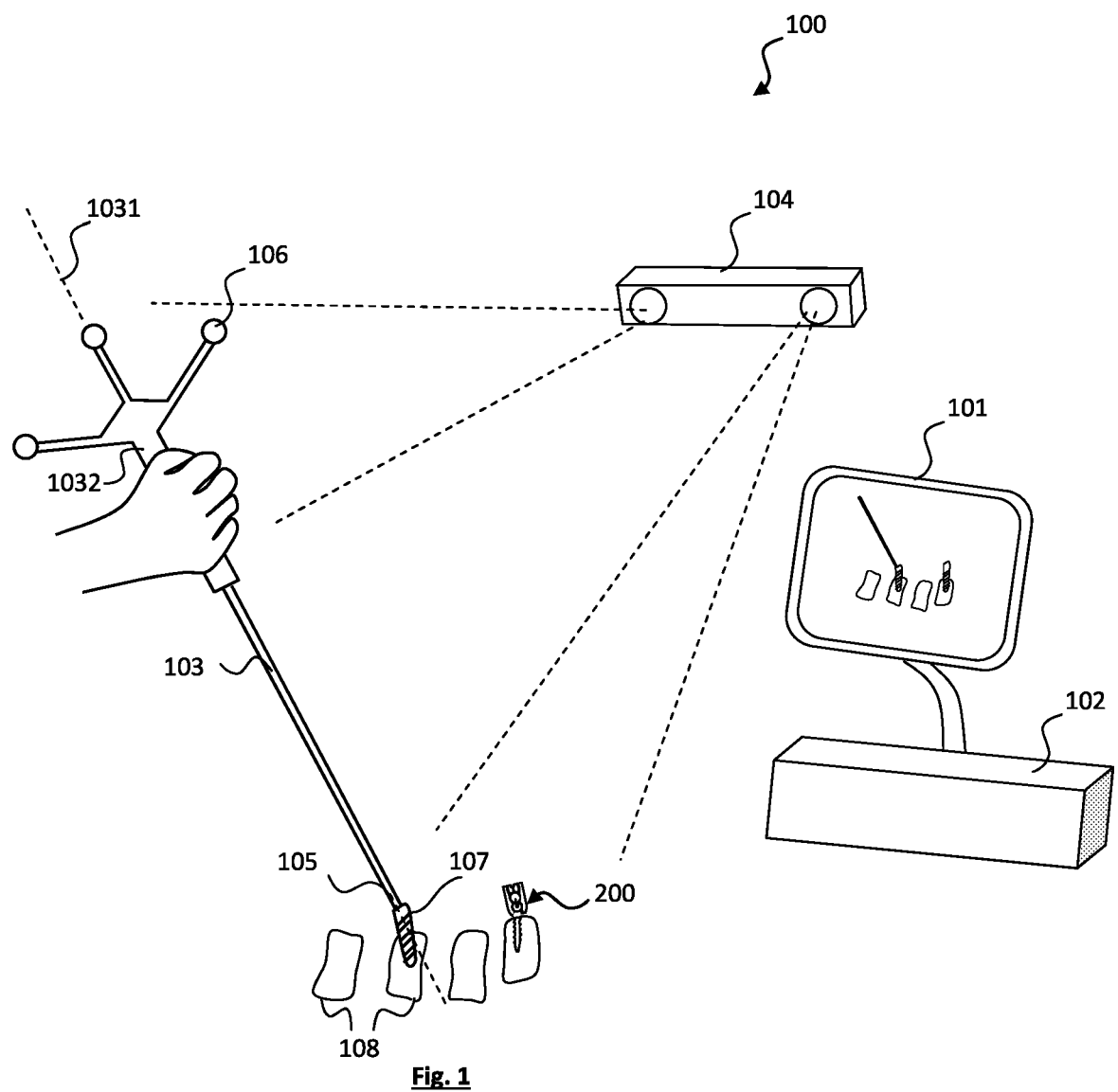
FIG. 1 shows a surgical navigation system according to an embodiment of the present disclosure.

A surgical navigation system 100, designed to aid a surgeon or surgical team performing corrective spinal surgery, is illustrated in FIG. 1. The system 100 comprises a display in the form of computer monitor 101 that serves to display CT images taken of a patient's spine by a CT imager and a processor 102 connected to the display.

The navigation system further comprises a navigation probe 103 and an infrared (IR) camera 104 that is connected to the processor 102 and used to monitor the position of the navigation probe 103. The monitoring can include monitoring of the orientation of the navigation probe 103 and the positioning of the tip 105 or other mating surfaces of the navigation probe 103, for example. One or more reflective components such as reflective balls 106 are located on the navigation probe 103. The reflective components 106 are designed to reflect light of a particular frequency, for example infrared (IR), such that the IR camera 104 can remotely detect the position (including orientation) of the probe 103. In use, the IR camera 104 is pointed at the whole operative site.

The navigation probe 103 is elongated along a probe axis 1031. The probe axis 1031 extends through a handle or grip portion 1032 of the probe 103 and through the tip 105 of the probe 103.

The navigation probe 103 can be used to detect the position of one or markers at the operative site, such as fiducial markers 107 mounted to vertebrae 108 of the spine. For example, when the tip 105 of the navigation probe 103 is touched on a fiducial marker 107, positional data for the probe 103 may be provided to the processor 102 which in turn can provide a data signal to update the display device 101. The update to the display device may include correctional data allowing for correcting alignment of the displayed CT image, including images of the fiducial screw 107, to match with the actual position of the one or more markers 107 on the patient. The update may also allow the position of new anatomical landmarks or additional devices such as pedicle screws to be added to the image.

Figure 2:
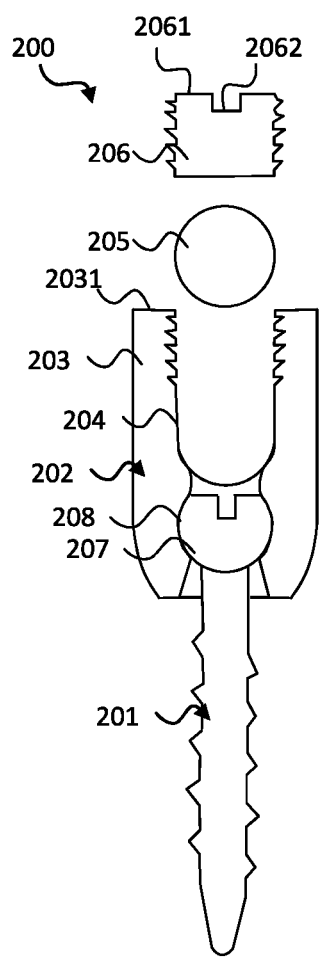
FIG. 2 shows an exploded cross-sectional view of a polyaxial bone screw according to an embodiment of the present disclosure.

One example of a device that may be probed to determine its position using the system navigation system 100 is a polyaxial bone screw 200, e.g. of a type used in spinal fusion surgery or otherwise. An example of a polyaxial bone screw 200 used in accordance with embodiments of the present disclosure is illustrated in FIG. 2. The polyaxial bone screw 200 includes a threaded shaft 201 for insertion in bone and a head 202 connected to the shaft 201. The head 202 includes a U-shaped head body 203 including a recess 204 that is adapted to receive a bone rod 205. The head 202 further includes a locking cap 206 operable, through threaded engagement with the head body 203, to bear down on a top surface of the rod 205 and lock the rod 205 in position in the recess 204.

Figure 3A:
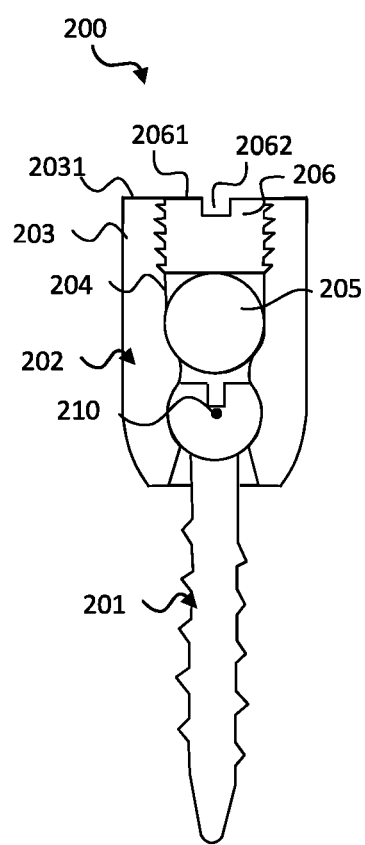
FIGS. 3a and 3b show cross-sectional views of the polyaxial bone screw of FIG. 2 at different rotation positions.
Figure 3B:
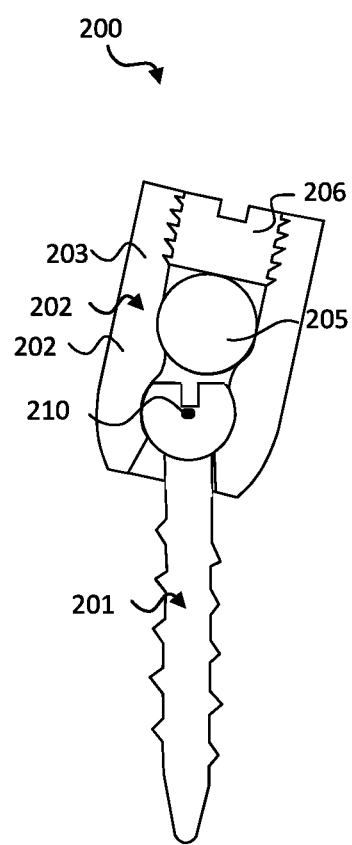

When the locking cap 206 bears against the rod 205, a top surface 2061 of the locking cap is substantially aligned with a top surface 2031 of the head body 203, as shown in FIGS. 3a and 3b. In this embodiment, a top surface of the head 202 of the bone screw 200 is therefore provided by a combination of a top surface 2031 of the U-shaped body and a top surface 2061 of the locking cap 206. The top surface 2061 of the locking cap includes a recess 2062 adapted to receive the head of a driver that drives the locking cap 206 into position.

At a top end of the shaft 201, the head 202 is connected to the shaft 201 by a polyaxial ball and socket joint. The joint comprises a spherical connector portion 207 integral with a top end of the shaft 201 and a conforming spherical recess portion 208 at a bottom end of the head body 203. The ball and socket joint enables the head 202 of the bone screw 200 to rotate relative the shaft 201 about a centre of rotation of the head 202 of the bone screw 200, the location of the centre of rotation being indicated by the dot 210 in the Figures. The head 202 can rotate by swivelling about the centre of rotation 210 and tilting about the centre of rotation 210.

When the shaft 201 of the screw 200 is inserted in bone, usually the only accessible part of the bone screw is the head 202. While the position of the shaft 201 remains substantially fixed relative to the bone, the head 202 is rotatable relative to the bone, as shown by comparing FIGS. 3a and 3b, for example. Therefore, using a navigation probe 103 to probe a point on the outside of the head 202 of the bone screw 200 does not necessarily provide an accurate indication of the position of the bone screw 200 (or at least the head 202 of the bone screw 200), relative to the bone, for all surgical navigation purposes. For example, it does not necessarily identify the location of the top of the shaft 201 of the bone screw 200, the position of which is fixed relative to the bone. Embodiments of the present disclosure enable positioning of the polyaxial bone screw 200 to be more accurately determined using a surgical navigation system 100 as described above, for example, through probing of the head 202 of the bone screw 200.

Figure 5:
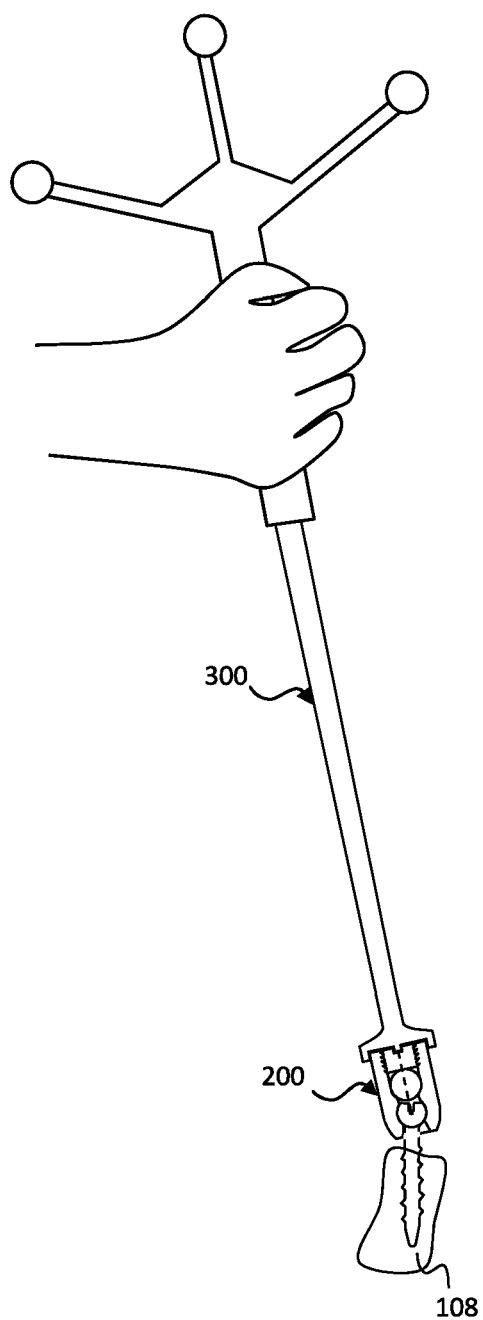
FIG. 5 shows a schematic view of a navigation probe engaged with the polyaxial bone screw of FIG. 2 when held by a surgeon.

Referring to FIGS. 4a and 4b, the top surface 2031, 2061 of the head 202 of the bone screw 200 provides a first mating surface 211 of the head 202 of the bone screw 200 and a distal end surface 301 at the tip 302 of a navigation probe 300 provides a second mating surface 301 adapted to engage the first mating surface 211 in a tight fit manner. The distal end surface 301 extends along a plane substantially perpendicular to the probe axis 304 of the probe 300. When the first and second mating surfaces 211, 301 are engaged, the first and second mating surfaces 211, 301 abut each other in a substantially parallel relationship. The first and second mating surfaces 211, 301 have only one clear position of engagement, where the first and second mating surfaces 211, 301 rest against each other with a tight fit. Engagement between the navigation probe 300 and the screw 200 is further illustrated in FIG. 5.

The engagement between the first and second mating surfaces 211, 301 is such that the navigation probe 300 takes up a predetermined orientation relative to the head 202 of the bone screw 200. Specifically in this embodiment, upon engagement, the orientation of the probe 300 is such that the probe axis 304 extends through the centre of rotation 210 of the bone screw 200.

The bone screw 200 and navigation probe 300 are therefore configured such that, when the first and second mating surfaces 211, 301 are engaged, at all rotational positions of the head 202 of the bone screw 200 relative to the shaft 201, the probe axis 304 has a fixed orientation relative to the head 202 of the bone screw 200, and the second mating surface 301 of the navigation probe 300 is at a constant distance from the centre of rotation 210 of the bone screw 200. This is evident from a comparison of FIGS. 4a and 4b, for example, which show the head 202 of the bone screw 200 in two different rotational positions.

The fixed orientation of the navigation probe 300 relative to the head 202 of the bone screw 200, when the first and second mating surfaces 211, 301 are engaged, enables the navigation system 100 to reliably determine the direction to the centre of rotation 210 of the bone screw 200 from the tip 302 of the navigation probe. Specifically, in this embodiment, through monitoring using the navigation system 100 of the positioning of the second mating surface 301 of the navigation probe 300 and the orientation of the probe axis 304, the axis in free space along which the centre of rotation 210 of the bone screw 200 lies can be determined. Moreover, through knowledge of the constant distance between the second mating surface 301 and the centre of rotation 210 of the bone screw (which is the substantially same as the distance between the first mating surface 211 and the centre of rotation 210 of the bone screw, when the two mating surfaces are engaged), the location of the centre of rotation 210 can be identified.

The identified location of the centre of rotation 210 of the bone screw may be treated as a reference point for the bone screw 200. The position of the reference point may be added or registered in the image on the display 101 of the navigation system 100, for example. Alternatively, the location of a different reference point may be determined and displayed, which different reference point has a fixed positional relationship with the centre of rotation of the head 202 of the bone screw.

Figure 6:
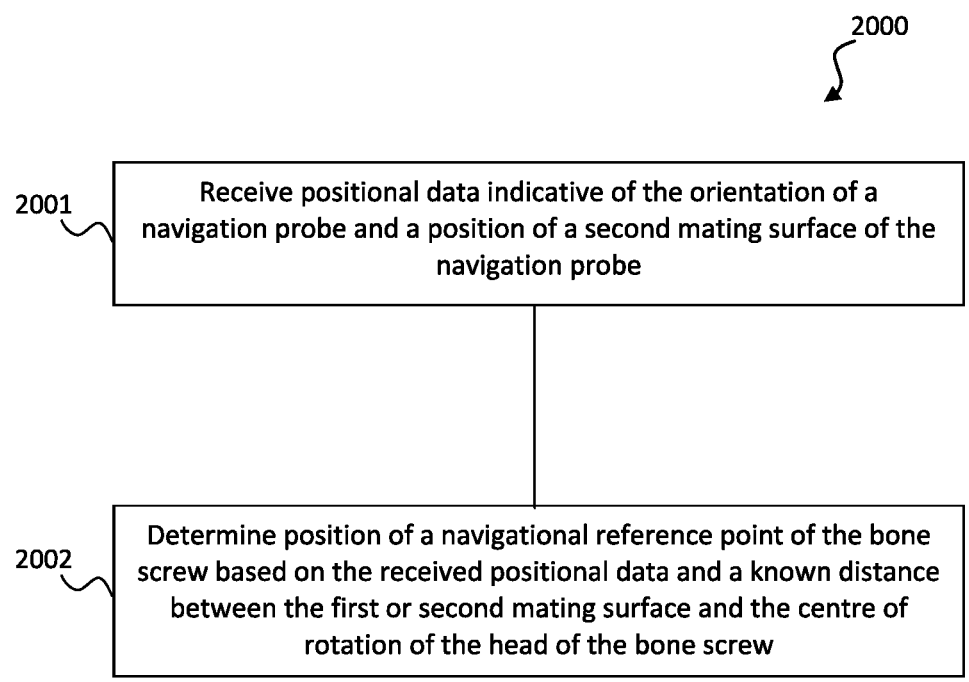
FIG. 6 shows a flowchart illustrating a method according to an embodiment of the present disclosure.

With reference to the flowchart 2000 of FIG. 6, and in accordance with the above discussions, in one embodiment, at item 2001, positional data is received indicative of the orientation of a navigation probe and a position of a second mating surface of the navigation probe, when the second mating surface is engaged with a first mating surface of the head of the bone screw. At item 2002, a position of a navigational reference point of the bone screw is determined based on the received positional data and a known distance between the first or second mating surface and the centre of rotation of the head of the bone screw. A machine-readable medium can be provided comprising instructions stored therein, which when executed by the processor 102, causes the processor 102 to perform the receiving and determining at 2001 and 2002.

The first and second mating surfaces 211, 301 comprise first and second complimentary interlocking features adapted to engage each other. In this embodiment, a first interlocking feature is provided by the recess 2062 at the top surface of the locking cap 206 and a second interlocking feature is provided by a protrusion 305 at a centre of the distal end surface 301 of the navigation probe 300. The protrusion 305 is adapted to locate in the recess 2062 in a snug fit manner.

The second mating surface 301 of the navigation probe includes an outer flange 306 that projects from a periphery of the second mating surface 301. The outer flange 306 is annular in this embodiment. The outer flange 306 is adapted to extend around a periphery of the first mating surface 211 when the first and second mating surfaces 211, 301 are engaged. The outer flange 306 defines a recess of the navigation probe 300 that receives the top of the head 202 of the bone screw 200 therein, when the first and second mating surfaces 211, 301 are engaged.

Figure 7A:
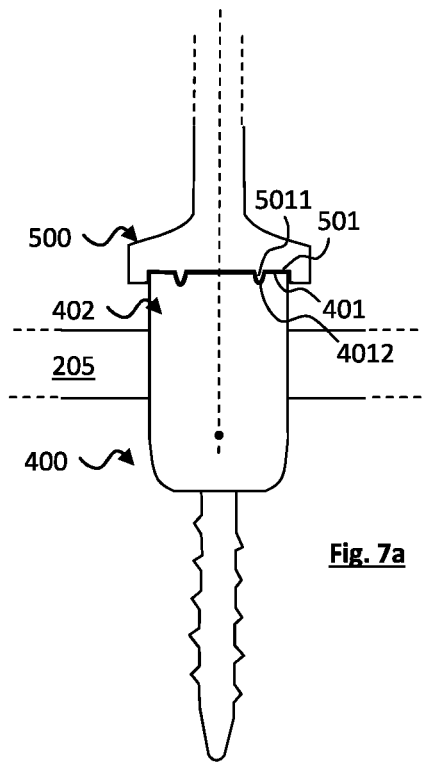
FIG. 7a shows a lateral view of a tip of a navigation probe engaged with a polyaxial bone screw according to another embodiment of the present disclosure.
Figure 7B:
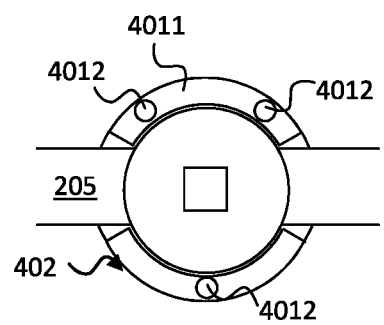

An alternative embodiment of the present disclosure is illustrated in FIGS. 7a and 7b. In this embodiment, engagement between a polyaxial bone screw 400 and a navigation probe 500 is achieved in substantially the same manner as described above except that a different configuration of interlocking features is provided at first and second mating surfaces 401, 501. In particular, at a first mating surface 401 of the head 402 of the screw, and particularly a substantially annular top surface 4011 of the head body, first interlocking features are provided in the form of three recess 4012, the recesses 4012 having a dimple-like form. The second mating surface 501 of the navigation probe 500 comprises second interlocking features in the form of three bumps 5011 that are arranged to extend into the three recesses 4012 when the first and second mating surfaces 401, 501 are engaged.

Figure 8:
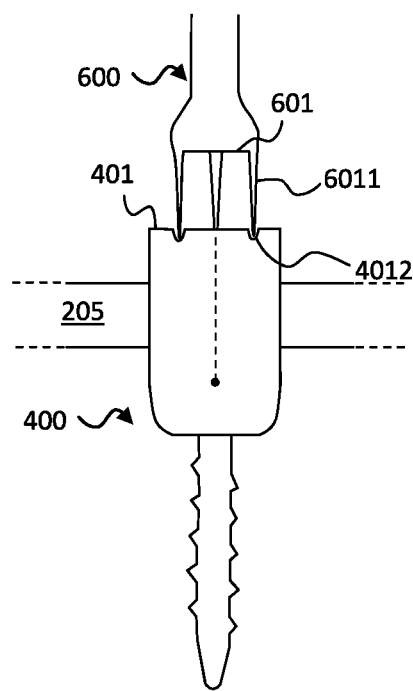
FIG. 8 shows a lateral view of a tip of a navigation probe engaged with a polyaxial bone screw according to another embodiment of the present disclosure.

In the preceding embodiments, first and second mating surfaces have relatively broad surface areas that abut against each other. Alternatively, separate, distinct points of engagement can be made between first and second mating surfaces. For example, in the embodiment illustrated in FIG. 8, a different navigation probe 600 is used in conjunction with the bone screw 400 of FIGS. 7a and 7b. In this embodiment, a second mating surface 601 of the navigation probe 600 has three extended protrusions 6011 that are adapted to extend into the three recesses 4012 of the bone screw 400, wherein the only contact between the navigation probe 600 and the bone screw 400 is via the protrusions 6011.

Figure 9:
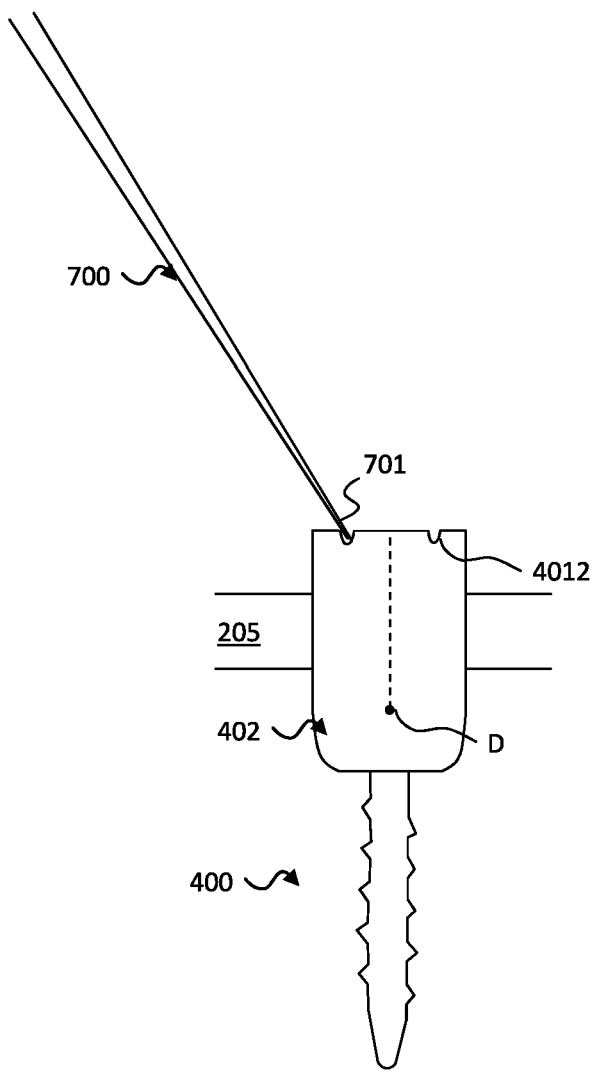
FIG. 9 shows a lateral view of a tip of a navigation probe engaged with a polyaxial bone screw according to another embodiment of the present disclosure.
Figure 10:
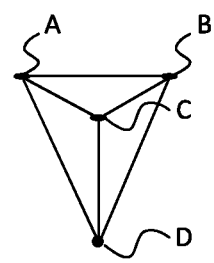
FIG. 10 shows an illustration of a triangulation calculation used to determine a location of a centre of rotation of the head of the polyaxial bone screw of FIG. 9.

While, in embodiments above, a reference point of the bone screw can be determined using a single engagement action between the navigation probe and the head of the bone screw, in alternative embodiments a similar result may be achieved through successive engagements between a navigation probe and different marker points on the head of the bone screw, generally as illustrated in FIG. 9. In this embodiment, the three recesses 4012 of the head of the bone screw 400 provide first, second and third marker points, respectively. The tip 701 of a navigation probe 700 is successively engaged with the marker points 4012 to determine, in conjunction with the apparatus of the navigation system, the locations of the marker points 4012. From the location of the marker points 4012, a reference point of the bone screw 400 can be determined. In particular, once the locations A, B and C of the first second and third marker points 4012 have been determined, the reference point can be determined based on a triangulation calculation, generally as represented in FIG. 10. The calculation is based on the determined locations A, B and C of the first, second and third marker points 4012 and a known, fixed spatial relationship between each of the first, second and third marker points 4012 and the centre of rotation D of the head 202 of the bone screw 200.

Figure 11:
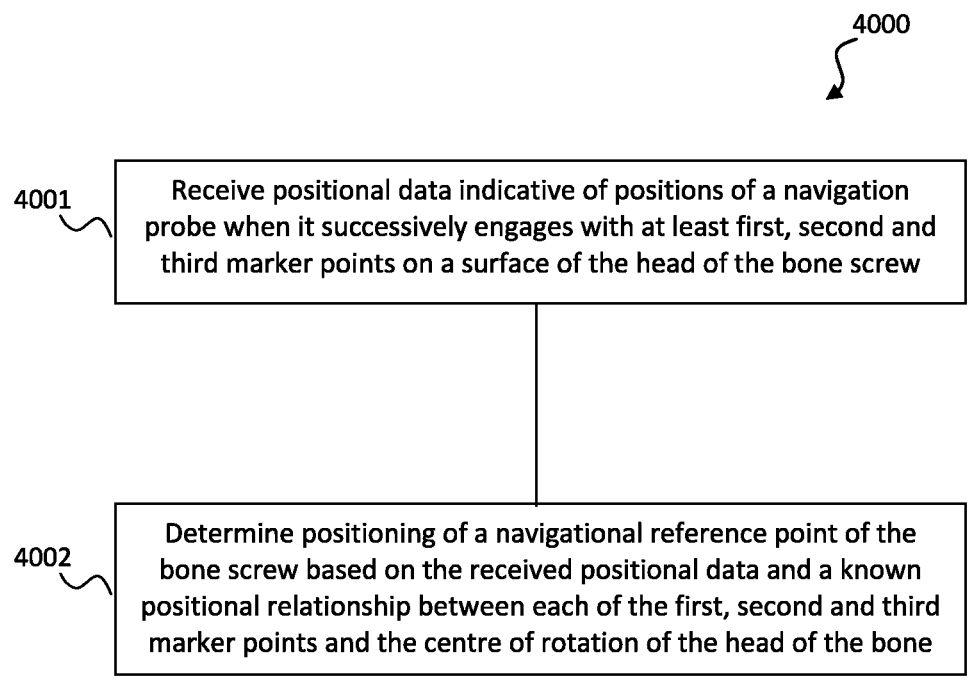
FIG. 11 shows a flowchart illustrating a method according to another embodiment of the present disclosure.

With reference to the flowchart 4000 of FIG. 11, and in accordance with the above discussions, in one embodiment, at item 4001, positional data is received indicative of positions of a navigation probe when it successively engages with at least first, second and third marker points on a surface of the head of the bone screw. At item 4002, a position of a navigational reference point of the bone screw is determined based on the received positional data and a known positional relationship between each of the first, second and third marker points and the centre of rotation of the head of the bone screw. A machine-readable medium can be provided comprising instructions stored therein, which when executed by the processor 102, causes the processor 102 to perform the receiving and determining at 4001 and 4002.

Figure 12A:
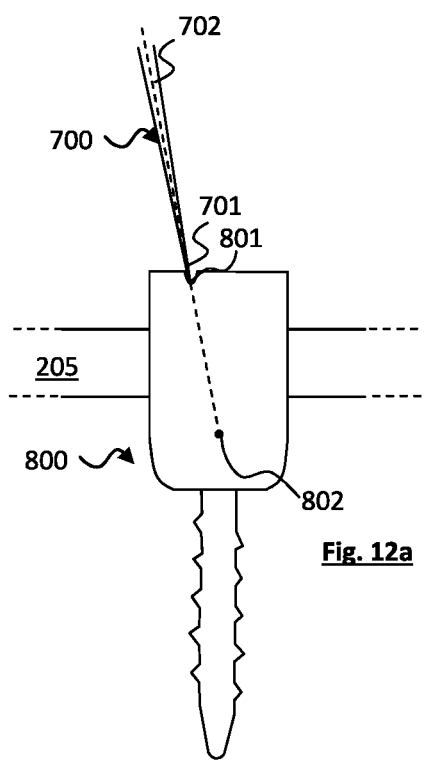
FIG. 12a shows a lateral view of a tip of a navigation probe engaged with a polyaxial bone screw according to another embodiment of the present disclosure.
Figure 12B:
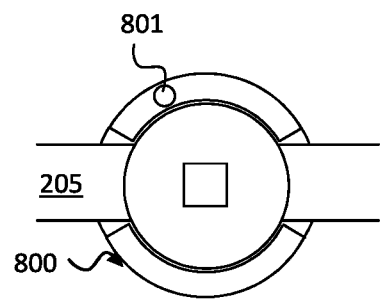

In the preceding embodiment, a reference point of the bone screw is determined through probing at least three marker points of the bone screw. However, in alternative embodiments a reduced number of marker points may be probed. For example, as illustrated in FIGS. 12a and 12b, in one embodiment a polyaxial bone screw 800 may have a first marker point only, provided by recess 801. An approximation of the location of the centre of rotation 802 of the bone screw 800 may be made from probing of the position of this single marker point 801. The reference point may be the centre of rotation 802 of the head of the bone screw 800, a reference point having a fixed positional relationship with the centre of rotation 802 or otherwise.

The surgeon in this embodiment is directed to hold the probe such that the probe axis 702 points roughly toward the centre of rotation 802 of the bone screw 800 when engaged with the first marker point 801. Thus, once the orientation of the probe 700 and the location of the first marker point 801 in free space is determined using the navigation system, and based on knowledge of the distance between the first marker point 801 and the centre of rotation 802 of the bone screw 800, the location of the centre of rotation 802 and thus the reference point can be estimated.

Figure 13:
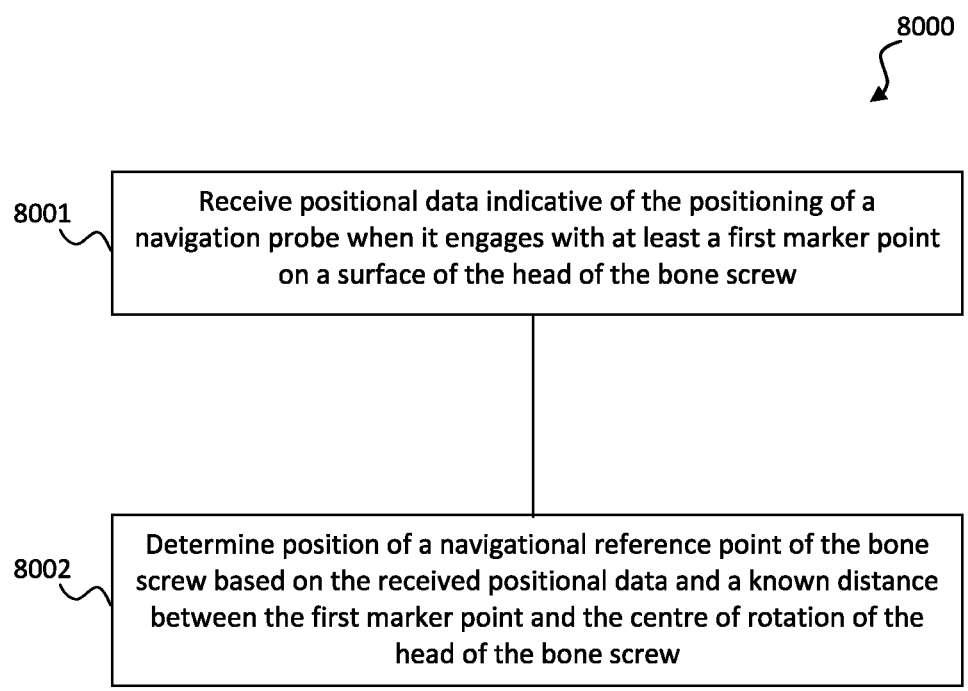
FIG. 13 shows a flowchart illustrating a method according to an embodiment of the present disclosure.

With reference to the flowchart 8000 of FIG. 13, and in accordance with the above discussions, in one embodiment, at item 8001, positional data is received indicative of the positioning of a navigation probe when it engages with at least a first marker point on a surface of the head of the bone screw. At item 8002, a position of a navigational reference point of the bone screw is determined based on the received positional data and a known distance between the first marker point and the centre of rotation of the head of the bone screw. A machine-readable medium can be provided comprising instructions stored therein, which when executed by the processor 102, causes the processor 102 to perform the receiving and determining at 8001 and 8002.

Figure 14:
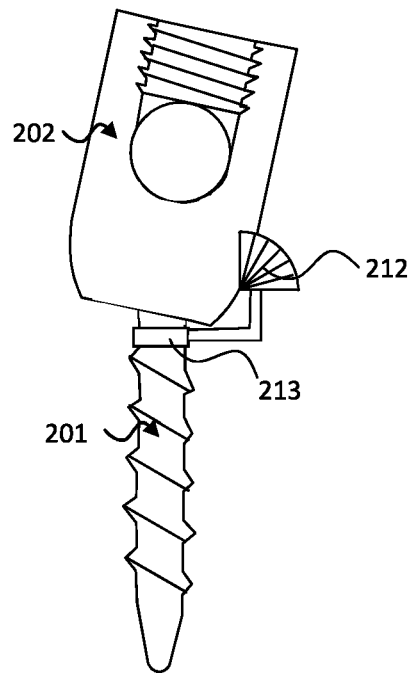
FIG. 14 shows a view of the bone screw of FIG. 2 in combination with an indexing device.

In embodiments described above, determining the location of the centre of rotation of the head of the bone screw and an associated reference point can enable an instantaneous analysis of screw positioning to be made (particularly adjacent the surface of bone, for example) and/or an analysis of movement of screw positioning over time to be made, using the surgical navigation system. The technique described may also be used to obtain an indication of the orientation of the head of the bone screw. However, in some instances, the techniques may not enable an indication of the orientation of the shaft of the bone screw to be accurately determined. To enable shaft orientation to be determined, an indexing device can be provided, as illustrated in FIG. 14, for example. The indexing device includes a protractor 212 or other type of angle measuring device. The indexing device is mounted via a collar 213 to the shaft 201 of the bone screw 200. The indexing device is releasable from the shaft 201 after use. The indexing device enables an angle between the head 202 of the bone screw and the shaft 201 to be determined.

Figure 15:
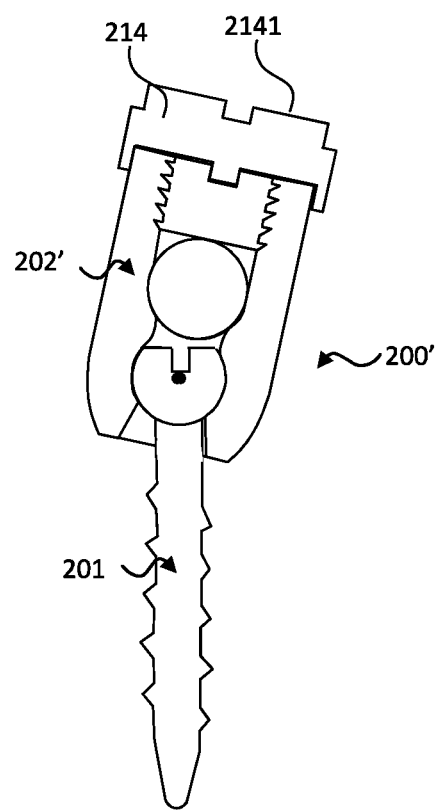
FIG. 15 shows a cross-sectional view of a polyaxial bone screw according to another embodiment of the present disclosure.

It will be appreciated by persons skilled in the art that numerous variations and/or modifications may be made to the above-described embodiments, without departing from the broad general scope of the present disclosure. Merely as one example, the bone screw 200 of FIGS. 2 to 3*b* may be modified in accordance with the bone screw 200' illustrated in FIG. 15. In this modification, the head 202' of the bone screw 200' comprises a releasable extension member 214 that locates on a base portion of the head 200' and provides a first mating surface 2141 of the head 202' of the bone screw 200' for the purpose of determining the positioning of the bone screw in accordance with methods of the present disclosure.

The present embodiments are, therefore, to be considered in all respects as illustrative and not restrictive.

The invention claimed is:

1. A surgical navigation system comprising:
   a polyaxial bone screw, the polyaxial bone screw comprising:
      a screw portion having a threaded shaft for insertion in bone and a connector at a top end of the threaded shaft, the connector having a spherical or part-spherical shape; and
      a head rotatably connected to the connector such that the head is rotatable relative to the screw portion in three axes about a centre point of rotation of the head, the centre point of rotation of the head defined by the spherical or part-spherical shape of the connector, wherein the head comprises a head body having a recess oriented and defined within the head body to receive a bone rod such that the bone rod extends in a direction that is substantially transverse to an axis of elongation of the threaded shaft;
   a navigation probe for probing the position of the polyaxial bone screw when the bone rod is received in the recess, the navigation probe having a probe axis;
   wherein the head of the polyaxial bone screw comprises a first mating surface and the navigation probe comprises a second mating surface adapted to engage the first mating surface,
   wherein the polyaxial bone screw and navigation probe are configured such that, when the first and second mating surfaces are engaged and the bone rod is received in the recess, all of the navigation probe is spaced from the centre point of rotation of the head of the polyaxial bone screw and at all rotational positions of the head of the polyaxial bone screw relative to the shaft:
      the probe axis of the navigation probe has a fixed orientation relative to the head of the polyaxial bone screw, and
      the second mating surface of the navigation probe is at a constant distance from the centre point of rotation.

2. The surgical navigation system of claim 1, wherein the second mating surface is provided at a distal end surface of the navigation probe.

3. The surgical navigation system of claim 2, wherein the second mating surface extends along a plane that is perpendicular to the probe axis.

4. The surgical navigation system of claim 1, wherein the first mating surface is provided by all or part of a top surface of the head of the polyaxial bone screw.

5. The surgical navigation system of claim 1, wherein the recess is U-shaped.

6. The surgical navigation system of claim 1, wherein the head comprises a locking cap operable to bear down on a top surface of the rod and lock the rod in position in the recess of the head body.

7. The surgical navigation system of claim 6, wherein the first mating surface comprises a top surface of the locking cap and a top surface of the head body.

8. The surgical navigation system of claim 1, wherein, when the first and second mating surfaces are engaged, the first and second mating surfaces abut each another in a substantially parallel relationship.

9. The surgical navigation system of claim 1, wherein the first and second mating surfaces comprise first and second complimentary interlocking features adapted to engage each other.

10. The surgical navigation system of claim 9, wherein the first complimentary interlocking features comprise recesses.

11. The surgical navigation system of claim 10, wherein the second complimentary interlocking features comprise protrusions.

12. The surgical navigation system of claim 9, wherein the first complimentary interlocking features are comprised in the first mating surface and the second complimentary interlocking features are comprised in the second mating surface.

13. The surgical navigation system of claim 1, wherein the second mating surface of the navigation probe comprises an outer flange that projects from a periphery of the second mating surface.

14. The surgical navigation system of claim 13, wherein the outer flange extends around a periphery of the first mating surface when the first and second mating surfaces are engaged.

15. A polyaxial bone screw, the polyaxial bone screw comprising:
   a screw portion having a threaded shaft for insertion in bone and a connector at a top end of the threaded shaft, the connector having a spherical or part-spherical shape; and
   a head rotatably connected to the connector such that the head is rotatable relative to the screw portion in three axes about a centre point of rotation of the head, the centre point of rotation of the head defined by the spherical or part-spherical shape of the connector, wherein the head comprises a head body having a recess configured to receive a bone rod such that the bone rod extends in a direction that is substantially transverse to an axis of elongation of the threaded shaft;
   the head of the polyaxial bone screw comprises a first mating surface adapted to engage a second mating surface of a navigation probe for probing a position of the polyaxial bone screw;
   wherein, when the first and second mating surfaces are engaged and the bone rod is received in the recess, all of the navigation probe is spaced from the centre point of rotation of the head of the polyaxial bone screw and at all rotational positions of the head of the polyaxial bone screw relative to the threaded shaft:
      the probe axis of the navigation probe has a fixed orientation relative to the head of the polyaxial bone screw, and
      the second mating surface of the navigation probe is at a constant distance from the centre point rotation.

16. A method of determining a position of a polyaxial bone screw during bone surgery using a surgical navigation system,
   wherein the polyaxial bone screw comprises:
      a screw portion having a threaded shaft inserted in bone and a connector at a top end of the threaded shaft, the connector having a spherical or part-spherical shape; and
      a head rotatably connected to the connector such that the head is rotatable relative to the screw portion in three axes about a centre point of rotation of the head, the centre point of rotation of the head defined by the spherical or part-spherical shape of the connector, wherein the head comprises:
   a head body having a recess defined in the head body to receive a bone rod such that the bone rod extends in a direction that is substantially transverse to an axis of elongation of the threaded shaft, and
   a first mating surface, and wherein the method comprises:

locating a bone rod in the recess of the head;

engaging a second mating surface of a navigation probe with the first mating surface of the head while the bone rod is located in the recess of the head, the engagement between the first and second mating surfaces being such that all of the navigation probe is spaced from the centre point of rotation of the head, a probe axis of the navigation probe has a fixed orientation relative to the head, and the second mating surface is at a constant distance from the centre point of rotation;

receiving positional data indicative of the orientation of the navigation probe and a position of the second mating surface of the navigation probe, when the second mating surface is in the engagement with the first mating surface of the head; and determining a position of a navigational reference point of the polyaxial bone screw based on the received positional data and a known distance between the first or second mating surface and the centre point of rotation of the head of the polyaxial bone screw.

17. A machine-readable medium comprising instructions stored therein, which when executed by a processor, causes the processor to perform the method of claim 16.

* * * * *